US00PP16317P2

(12) United States Plant Patent
Olesen

(10) Patent No.: US PP16,317 P2
(45) Date of Patent: Mar. 7, 2006

(54) MINIATURE ROSE PLANT NAMED 'POULHI019'

(50) Latin Name: *Rosa hybrida*
Varietal Denomination: Poulhi019

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 45 days.

(21) Appl. No.: 10/961,002

(22) Filed: Oct. 7, 2004

(51) Int. Cl.
*A01H 5/00* (2006.01)

(52) U.S. Cl. ..... Plt./118

(58) Field of Classification Search ..... Plt./118, Plt./125

See application file for complete search history.

*Primary Examiner*—Howard J. Locker

(57) ABSTRACT

A new miniature rose plant which has abundant, medium yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'Poulhi019'.

SUMMARY OF THE INVENTION

The present invention constitutes a new and distinct variety of miniature rose plant which originated from a controlled crossing between the female parent 'Poulcoo', a non-patented variety created by the same inventors, and the male parent, an unnamed seedling, also created by the same inventors. The two parents were crossed and the resulting seeds were planted in a controlled environment. The new variety named 'Poulhi019', was a selection of the resulting seedlings.

The new rose may be distinguished from its seed parent, 'Poulcoo', by the following combination of characteristics:

1. 'Poulhi019' has smaller flowers than those of 'Poulcoo'.
2. 'Poulhi019' has medium yellow flowers, while those of 'Poulcoo' are deep yellow.

The new variety may be distinguished from its pollen parent, an unnamed seedling, by the following combination of characteristics:

1. The unnamed seedling plant is less compact than 'Poulhi019'.
2. 'Poulhi019' has fewer flower petals than the unnamed seedling.

The objective of the hybridization of this rose variety for commercial culture was to create a new and distinct variety with unique qualities, such as:

1. Uniform and abundant yellow flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulhi019' from all other varieties of which he is aware.

As part of the rose development program, Mogens N. Olesen germinated the seeds from the aforementioned hybridization and conducted evaluations on the resulting seedlings in a controlled environment in Fredensborg, Denmark.

'Poulhi019' was selected by the inventor as a single plant from the progeny of the hybridization in 1999.

Asexual reproduction of 'Poulhi019' by cuttings and traditional budding was first done by Mogens N. Olesen in the nursery in Fredensborg, Denmark in July of 2000. This initial and other subsequent asexual propagations conducted in controlled environments have demonstrated that the characteristics of 'Poulhi019' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulhi019'. Specifically illustrated in the drawing:

FIG. 1.1; Flower buds at progressive stages of opening;

FIG. 1.2; Open flower viewed from above;

FIG. 1.3; Flower petals, detached;

FIG. 1.4; Sepals, receptacle, and pedicel;

FIG. 1.5; Bare stem exhibiting thorns;

FIG. 1.6; Juvenile leaves exhibiting anthocyanin;

FIG. 1.7; Mature leaves.

DETAILED DESCRIPTION OF THE VARIETY

The following is a description of 'Poulhi019', as observed in its growth in Burlington, Ontario. Observed plants are 4 months of age, and have been cultivated in 15 cm pots. Color references are made using The Royal Horticultural Society (London, England) Colour Chart, 2001, except where common terms of color are used.

For a comparison, several physical characteristics of the rose variety 'Poulhi019', a rose variety from the same inventor described and illustrated in U.S. Plant Pat. No. 15,041 issued on Jul. 27, 2004 are compared to 'Poulhi019' in Chart 1.

CHART 1

| | 'POULhi018' | 'POULhi019' |
|---|---|---|
| Petal Count | 50 | 31 |
| Petal size | 21 mm long<br>19 mm wide | 30 mm length<br>30 mm wide |
| Outer Petal Color, Upper Side | Yellow 2D | Yellow 4C |
| Diameter of open flower | 45 mm | 60 to 70 mm |

FLOWER AND FLOWER BUD

Blooming habit: Continuous.

Flower bud:

*Size.*—Upon opening, 20 mm in length from base of receptacle to end of bud. 13 mm in diameter.

*Bud form.*—Ovate.

*Bud color.*—As sepals unfold petals are Yellow Group 2C with occasional marginal intonations of Orange-Red Group 34A.

*Sepals.*—Upper Surface: Color: Green Group 138 B. Texture: Moderately pubescent. Lower Surface: Color: Yellow Green Group 144 A. Texture: Smooth to somewhat rough with scant stipitate glands. Shape: Sepal apex is cirrhose. Base is flat at union with receptacle. Margins: Margins have medium foliaceous appendages on three of the five sepals. Size: 23 mm long by 11 mm wide.

*Receptacle.*—Texture: Smooth. Shape: Urn-shaped. Size: 7 mm in height by 6 mm wide. Color: Yellow Green Group 144 B.

*Peduncle.*—Surface: Somewhat rough with few stipitate glands. Length: 30 mm average length. Diameter: 3.5 mm. Color: Yellow-Green Group 144 B. Strength: Upright, medium strength.

*Borne.*—Singularly.

Flower bloom:

*Fragrance.*—Light floral.

*Duration.*—As a pot plant, flowers last from 15 to 18 days.

*Size.*—Average flower diameter is 60 to 70 mm when open. Flower depth is 25 mm.

*Form.*—Upon opening, flower petals remain tightly packed and are slightly reflexing. Flowers open to form a rosette with overlapping petals of different sizes.

*Shape of flower when viewed from the side.*—Upon opening, upper part: flat. Upon opening, lower part: flattened convex. Open flower, upper part: flattened convex. Open flower, lower part: concave.

*Petalage.*—Average range: 31 petals total, with 15 petaloids.

Flower color:

*Upon opening, petals.*—Outermost petals: Upper Surface: Yellow Group 8B. Lower Surface: Yellow Group 4C. Occasionally, there are distinct intonations of the color of Red Group 38B at the marginal apex of the petal. Innermost petals: Upper Surface: Yellow Group 8B with light intonations of Orange 26A at the margins. Lower Surface: Yellow Group 4C with light intonations of Orange Group 29 A at margins.

*Upon opening, basal petal spots.*—Outer and inner petals: Upper Surface: Yellow Group 5A. Lower Surface: No distinctive coloration observed.

*After opening, petals.*—Outermost petals: Upper Surface: Yellow Group 4C. Lower Surface: Yellow Group 4C. Occasionally, intonations of Red Group 38B are present at the marginal apex of the petal. Innermost petals: Upper Surface: Yellow Group 4C. Lower Surface: Yellow Group 4C.

*After opening, basal petal spots.*—No distinctive coloration at the petal base observed.

General tonality: On open flower Yellow Group 4C. No change in tonality as flowers mature.

Petals:

*Petal reflex.*—Petals are moderately reflexed.

*Petal margin.*—Normally entire. On occasion there is a point at the center of the margin.

*Shape.*—Generally narrow elliptical. Base Shape is obtuse. Apex Shape is rounded.

*Size.*—On average, 30 mm in length by 30 mm wide.

*Thickness.*—Average.

*Arrangement.*—Not formal.

Petaloids:

*Quantity.*—15 on average.

*Size.*—12 mm long by 5 mm wide.

*Shape.*—Irregular to narrow elliptic.

*Color.*—Yellow Group 4C on both upper and lower surfaces.

Reproductive organs:

*Pollen.*—None observed.

*Anthers.*—Size: 3 mm in length. Color: Yellow Group 12A to 12B. Quantity: 70 on average.

*Filaments.*—Color: Yellow Group 12A. Length: 5–7 mm.

*Pistils.*—Length: 10 mm long. Quantity: 60 on average.

*Stigmas.*—Superior relative to the length of the filaments and the height of the anthers. Color: Greyed-Yellow Group 160A.

*Styles.*—Color: Red-Purple Group 58B.

*Seed formation.*—Not observed.

PLANT

Plant growth: Vigorous, compact, upright to bushy. When grown as a 15 cm pot plant on its own roots, the average height of the plant itself is 20 cm and the average width is 20 cm.

Stems:

*Color.*—Young wood: Yellow-Green Group 144B. Older wood: Yellow-Green Group 144B.

*Internodes.*—On average, there are 23 mm between nodes.

*Length of stems.*—On average, canes are 17 cm from the base of the plant to the flowering portion.

*Diameter of stem.*—3 mm average.

*Surface texture.*—Young wood: Smooth. Older wood: Smooth.

Thorns:

*Incidence.*—10 mm per 10 cm of stem.

*Size.*—Average length is 5 mm.

*Color.*—Juvenile thorns are Greyed-Orange Group 173A. More mature thorns exhibit Greyed-Orange Group 173A to Greyed-Yellow Group 160B.

*Shape.*—Linear.

Plant foliage: The normal number of leaflets on normal leaves in middle of the stem varies from 5 to 7 leaflets.

*Compound leaf size.*—90 (l)×65 mm (w).

*Quantity.*—4 leaves per 10 cm of stem.

*Color.*—Juvenile foliage: Upper Leaf Surface is Yellow-Green Group 144A. At the margins, anthocyanic pigments the color of Greyed-Red Group 178A observed. Lower Leaf Surface is Green Group 144B. Mature foliage: Upper Leaf Surface is Yellow-Green Group 147A. Lower Leaf Surface is Yellow-Green Group 147C.

Plant leaves and leaflets:

*Stipules.*—Size: 10 mm in length. Shape: Linear, slightly broad based with outward extending apices. Margins: Finely serrated with many stipitate glands. Color: Green Group 138 A.

*Petiole.*—Length: 13 mm. Diameter: 1.5 mm on average. Color: Upper surface is Yellow-Green Group 146B. Lower surface is Yellow-Green Group 144B. Margins: Few stipitate glands observed.

*Rachis.*—Size: 32 mm in length. Color: Upper surface is Yellow-Green Group 146B. Lower surface is Yellow-Green Group 144B. Underneath: Small prickles normally located mid-way between leaflets. Margins: Few stipitate glands observed.

*Leaflet.*—Size: 36 mm in length by 25 mm wide. Edge: Serrate. General Shape: Elliptical to somewhat rounded. Apex Shape: Acuminate to slightly mucronate. Base Shape: Round. Texture: Smooth. Thickness: Average to somewhat thin. Arrangement: Odd pinnate. Venation: Reticulate. Leaf Gloss: Matte appearance.

Disease resistance: Average resistance to mildew, black sport, and *Botrytis* under normal glasshouse growing conditions in Burlington, Ontario, and Fredensborg, Denmark.

It is claimed:

1. A new and distinct variety of rose plant of the miniature class named 'Poulhi019', illustrated and described herein, due to its abundant, medium yellow flowers, vigorous growth, compact habit, suitability for production from softwood cuttings in pots, and durable flowers and foliage which make the variety suitable for distribution in the floral industry.

* * * * *

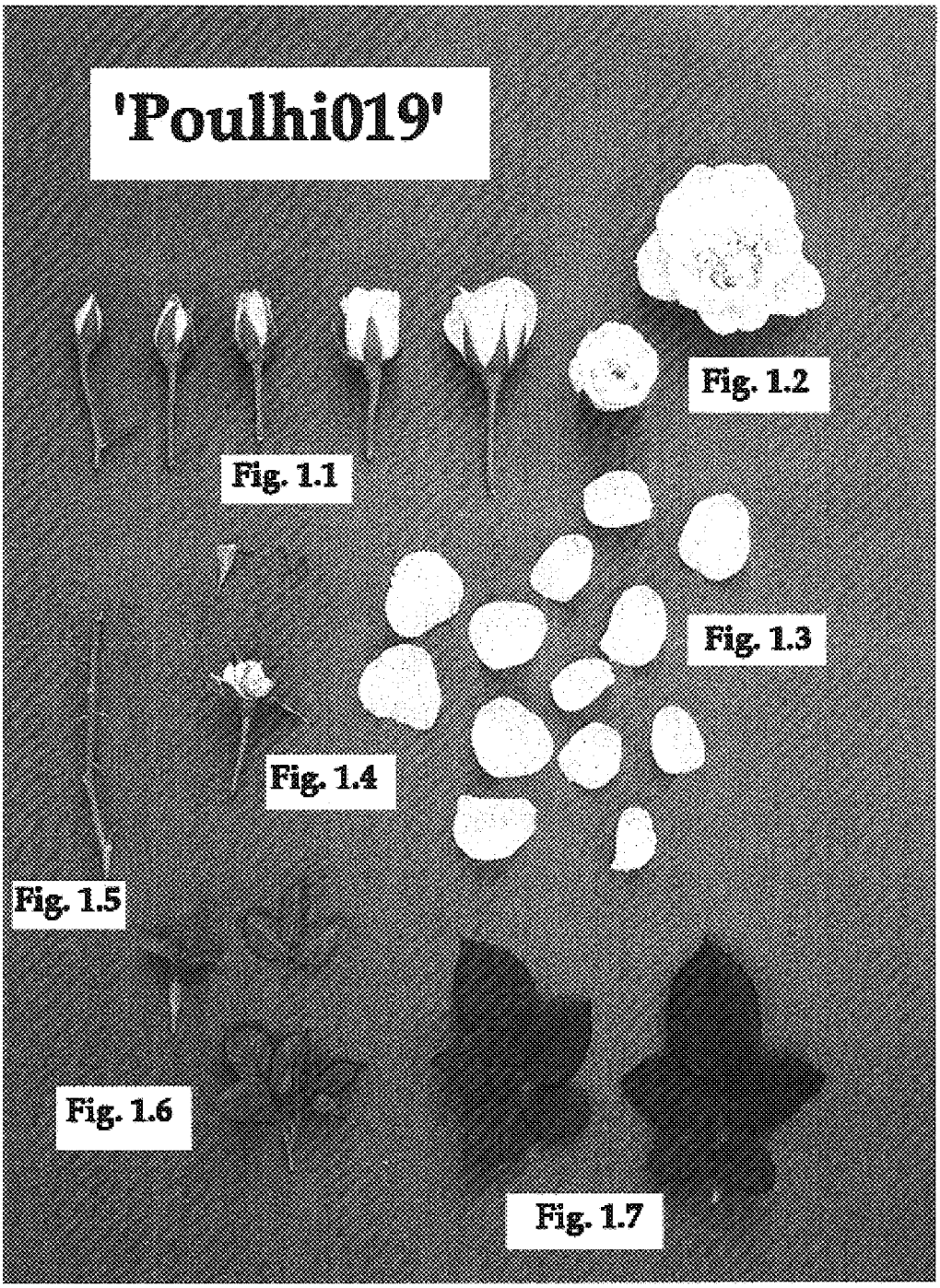
'Poulhi019'
Fig. 1.1
Fig. 1.2
Fig. 1.3
Fig. 1.4
Fig. 1.5
Fig. 1.6
Fig. 1.7